United States Patent

[19]

Hafele

[11] Patent Number: 6,000,218
[45] Date of Patent: Dec. 14, 1999

[54] SYSTEM FOR MONITORING THE FUNCTIONING ABILITY OF CATALYTIC CONVERTERS AND/OR LAMBDA SENSORS

[75] Inventor: Edelbert Hafele, Karlsruhe, Germany

[73] Assignee: Heraeus Electro-Nite International N.V., Houthalen, Belgium

[21] Appl. No.: 08/836,702

[22] PCT Filed: Nov. 21, 1995

[86] PCT No.: PCT/EP95/04584

§ 371 Date: May 19, 1997

§ 102(e) Date: May 19, 1997

[87] PCT Pub. No.: WO96/16257

PCT Pub. Date: May 30, 1996

[30] Foreign Application Priority Data

Nov. 22, 1994 [DE] Germany ............................ 44 41 432

[51] Int. Cl.⁶ ........................................................ F01N 3/00
[52] U.S. Cl. .............................. 60/276; 60/277; 60/274; 60/285; 123/688; 123/691
[58] Field of Search .............................. 60/274, 276, 285, 60/289, 277; 123/688, 691; 701/709

[56] References Cited

U.S. PATENT DOCUMENTS 5,060,474 10/1991 Aramaki ................................... 60/277
5,103,640 4/1992 Nada et al. ............................... 60/274
5,105,651 4/1992 Gutmann ............................... 73/23.31
5,265,417 11/1993 Visser et al. ............................. 60/274
5,291,673 3/1994 Hamburg et al. ........................ 60/274
5,357,749 10/1994 Ohsuga et al. .......................... 60/274

FOREIGN PATENT DOCUMENTS 4039429 6/1992 Germany ................................. 27/416
4211116 10/1993 Germany ..................................... 77/8

Primary Examiner—Thomas E. Denion
Assistant Examiner—Binh Tran
Attorney, Agent, or Firm—Antonelli, Terry, Stout & Kraus, LLP

[57] ABSTRACT

A system for monitoring the operatibility of catalytic converters and/or lambda probes in exhaust gas detoxification systems. It is characterised in that a pollutant sensor is placed downstream of (in relation to the exhaust gas stream) or in the catalytic converter, in that the lambda value and/or oxygen content of the exhaust gas are altered by a specific amount either by the engine or by a device, and in that the electrical output signal from the pollutant sensor is compared in a comparator circuit to a value curve stored in a storage unit and corresponding to the defined alteration of the lambda value.

12 Claims, 1 Drawing Sheet

SYSTEM FOR MONITORING THE FUNCTIONING ABILITY OF CATALYTIC CONVERTERS AND/OR LAMBDA SENSORS

BACKGROUND OF THE INVENTION

The invention relates to a system for monitoring the functional ability of catalytic converters and/or lambda sensors in detoxification systems for exhaust.

Systems of this kind are known especially for exhaust from internal combustion engines in a plurality of embodiments (for example DE 23 04 464 C2).

These known systems suffer from the disadvantages that they cannot monitor functional ability sufficiently reliably since indirect measurement is performed either with two lambda sensors (DE 40 39 429) or by temperature probes. In particular, reliable determination of functional ability is not possible in aged catalytic converters because of the conversion rate of hydrocarbons and other pollutants that no longer correlate with the oxygen storage capacity.

A device is also known (DE 42 11 116) with which the lambda value of a mixture can be modulated to determine the functional ability of the catalytic converter in such fashion that an oxygen excess periodically alternates with an oxygen deficiency. On the basis of the sudden reaction of a lambda sensor located downstream from the catalytic converter in the flow direction, the functional ability and/or degree of conversion capacity of the catalytic converter is detected. Here again the indirect acquisition of information about the function of the catalytic converter is disadvantageous.

SUMMARY OF THE INVENTION

Hence the goal of the invention is to design a system for monitoring the functional ability of catalytic converters and/or lambda sensors in detoxification systems for exhaust that reacts more reliably as well as rapidly.

This goal is achieved according to the invention in a system according to the species in accordance with the preamble of the main claim, by virtue of its characterizing features.

Thus, according to the present invention it is not a lambda sensor or a temperature sensor that is provided for monitoring, but an emission sensor in the flow direction of the exhaust, downstream from or in the catalytic converter. In addition, a rapid, defined change in the load and/or the rpm of an engine or of the lambda value and/or the oxygen content in the exhaust is performed, for example by defined leaning out or enrichment of the exhaust from internal combustion engines according to a specific procedure or cycle and the electrical output signal from the emission sensor is compared with a value profile that is stored and corresponds to the defined change in lambda value. If the electrical output signal lies within a certain tolerance range in the stored value profile, it is assumed that both the catalytic converter and the lambda sensors are in a functioning state. If the values fall outside a tolerance range, it provides an indirect indication of a defect in either the catalytic converter or the lambda sensors. Advantageously, the defined change in lambda value can occur by adding secondary air in the flow direction upstream from the catalytic converter so that its function and/or that of the emission sensor itself can be checked as well. Otherwise, only the function of the emission sensor itself is determined.

Advantageously it is also possible to locate the emission sensor between two or more individual catalytic converters because then the defined change reaches higher values of the emission peaks, but these comparatively higher concentrations can be reduced in the catalytic converter located downstream so that determination of the functional ability does not result in an increased emission figure.

BRIEF DESCRIPTION OF THE DRAWINGS

One preferred embodiment will now be described in greater detail with reference to the drawing, which provides a schematic diagram.

DETAILED DESCRIPTION OF THE PREFERRED EMBODIMENTS

Figure 1:
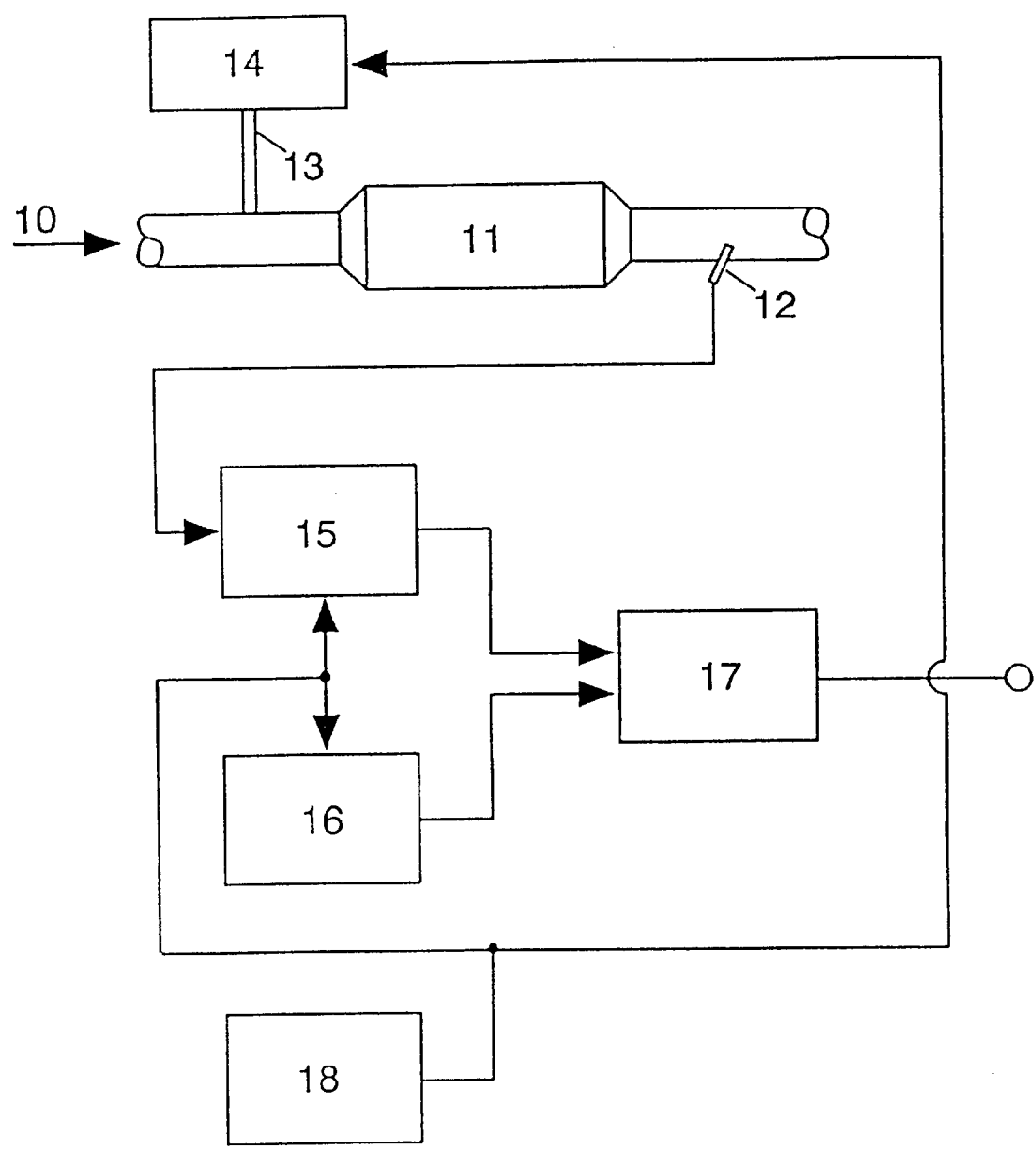

Initially, direction arrow 10 indicates the exhaust flowing from an internal combustion engine of a motor vehicle, which passes through a catalytic converter designated by 11 as a whole. Reference numeral 12 refers to an emission sensor located in flow direction 10 of the exhaust downstream from catalytic converter 11, said sensor responding for example to hydrocarbons HC. Between catalytic converter 11 and emission sensor 12 there is a line 13 through which air or pure oxygen, controlled to a specified degree, for example by a secondary air pump, can be supplied by the device designated as a whole by 14.

The output of emission sensor 12 is connected electrically with an evaluation circuit 15. Its outlet as well as the outlet of a memory 16 are connected with the inputs of a comparison circuit designated as a whole by 17, whose output signal provides information about the functional ability of catalytic converter 11 or the lambda sensors (not shown). A process control designated by 18 as a whole is connected with both device 14 and evaluation circuit 15 and memory 16.

By virtue of process control, firstly a preferably rapid defined change, namely a defined addition of secondary air, is effected that corresponds to a leaning out of the fuel-air mixture. At the same time, evaluation circuit 15 is activated for emission sensor 12 and reservoir 16 in order to compare the processed output signal of emission sensor 12 at the output of evaluation circuit 15 with a value profile corresponding to the defined change in lambda value, stored previously and located in comparison circuit 17. If the values match, or if they fall within a presettable tolerance range, it can be concluded that the catalytic converter and the lambda probes are functioning properly. If they fall outside this range, a defect must be assumed to exist.

I claim:

1. A system for monitoring a functional ability of at least one of catalytic converters and lambda sensors in detoxification systems for exhaust, comprising an emission sensor, the emission sensor not being a lambda sensor and being located in a flow direction of the exhaust downstream from or in a catalytic converter; a device for effecting a defined change in lambda value in the exhaust upstream of the catalytic converter; and a comparison circuit for comparing an electrical output signal of the emission sensor with a value profile stored in memory and corresponding to the defined change in lambda value.

2. System according to claim 1, wherein the emission sensor is a HC sensor.

3. System according to claim 1, wherein the device for effecting the defined change in lambda value is a secondary air pump for pumping air into the exhaust upstream of the catalytic converter.

4. System according to claim 1, wherein the catalytic converter is connected to an exhaust from an internal combustion engine of a motor vehicle.

5. System according to claim 4, wherein the device for effecting the defined change in the lambda value is a device for changing at least one of rpm and load on the engine.

6. A method for monitoring a functional ability of at least one of a catalytic converter and a lambda sensor in a detoxification system for exhaust, comprising the steps of:

effecting a defined change in lambda value in the exhaust upstream of a catalytic converter;

obtaining an electrical output signal from an emission sensor provided downstream of the catalytic converter, the emission sensor not being a lambda sensor;

comparing the electrical output signal from the emission sensor with a value profile stored in a memory and corresponding to the defined change in lambda value; and based on a result of the step of comparing, determining whether the catalytic converter and/or lambda sensor is functioning properly.

7. A method according to claim 6, wherein the step of effecting the defined change is performed cyclically.

8. A method according to claim 6, wherein the step of effecting the defined change is performed as a simulated malfunction of the catalytic converter as a result of at least one of a rapid enrichment and a rapid leaning out of the mixture.

9. A method according to claim 6, wherein the rapid leaning out of the mixture is caused by adding secondary air to the exhaust.

10. A method according to claim 6, wherein the emission sensor is a HC sensor.

11. A method according to claim 6, wherein the step of effecting the defined change in lambda value comprises introducing secondary air into the exhaust upstream of the catalytic converter.

12. A method according to claim 6, wherein the exhaust is exhaust from an internal combustion engine of a motor vehicle and the step of effecting the defined change in lambda value comprises changing at least one of rpm of and load on the engine.

* * * * *